(12) United States Patent
Capet et al.

(10) Patent No.: US 12,145,916 B2
(45) Date of Patent: Nov. 19, 2024

(54) POLYMORPH FORM OF PITOLISANT HYDROCHLORIDE

(71) Applicant: Bioprojet PHARMA, Paris (FR)

(72) Inventors: Marc Capet, Melesse (FR); Morgan Pauchet, Mont Saint Aignan (FR)

(73) Assignee: Bioprojet PHARMA, Paris (FR)

( * ) Notice: Subject to any disclaimer, the term of this patent is extended or adjusted under 35 U.S.C. 154(b) by 0 days.

(21) Appl. No.: 18/621,972

(22) Filed: Mar. 29, 2024

(65) Prior Publication Data

US 2024/0327366 A1    Oct. 3, 2024

Related U.S. Application Data

(60) Provisional application No. 63/493,500, filed on Mar. 31, 2023.

(51) Int. Cl.
*C07D 295/088* (2006.01)
*A61K 31/4453* (2006.01)

(52) U.S. Cl.
CPC ...... *C07D 295/088* (2013.01); *A61K 31/4453* (2013.01)

(58) Field of Classification Search
CPC .................................................. C07D 295/088
See application file for complete search history.

(56) References Cited

U.S. PATENT DOCUMENTS

| | | | |
|---|---|---|---|
| 7,138,413 B1 | 11/2006 | Schwartz et al. |
| 7,169,928 B2 | 1/2007 | Schwartz et al. |
| 7,910,605 B2 | 3/2011 | Schwartz et al. |
| 8,207,197 B2 | 6/2012 | Raga et al. |
| 8,354,430 B2 | 1/2013 | Raga et al. |
| 8,486,947 B2 | 7/2013 | Schwartz et al. |
| 11,623,920 B2 | 4/2023 | Venkatragavan et al. |
| 11,945,788 B2 | 4/2024 | Venkatragavan et al. |
| 2022/0402886 A1 | 12/2022 | Venkatragavan et al. |

FOREIGN PATENT DOCUMENTS

| | | |
|---|---|---|
| WO | 2000006254 A2 | 2/2000 |
| WO | 2006084833 A1 | 8/2006 |
| WO | 2006103546 A2 | 10/2006 |

OTHER PUBLICATIONS

Apelt, J., et al, "Development of a New Class of Nonimidazole Histamine H3 Receptor Ligands with Combined Inhibitory Histamine N-Methyltransferase Activity" J. Med. Chem (2002) 45:1128-1141.

Meier, G., et al, "Influence of imidazole replacement in different structural classes of histamine H3-receptor antagonists", European Journal of Pharmaceutical Sciences (2001) 13:249-259.

Schwartz, J., "The histamine H3 receptor: from discovery to clinical trials with pitolisant", British Journal of Pharmacology (2011) 163:713-721.

Caira, Mino, "Crystalline Polymorphism of Organic Compounds", Topics in Current Chemistry (1998) 198:163-208.

International Search Report and Written Opinion of the International Search Authority, mailed on Jul. 3, 2024 in PCT/IB2024/000139.

*Primary Examiner* — Shawquia Jackson
(74) *Attorney, Agent, or Firm* — Hogan Lovells US LLP

(57) ABSTRACT

The present disclosure relates generally to a new crystalline form (i.e., polymorph) of pitolisant hydrochloride (Form II), pharmaceutical compositions comprising Form II, dosage forms comprising Form II, and methods of treating a disease or disorder with Form II, or with a pharmaceutical composition or dosage form comprising Form II.

15 Claims, 5 Drawing Sheets

POLYMORPH FORM OF PITOLISANT HYDROCHLORIDE

RELATED APPLICATIONS

This application claims the benefit of U.S. Provisional Application No. 63/493,500, filed on Mar. 31, 2023, the entire contents of which is incorporated herein by reference.

BACKGROUND

Polymorphism is an important consideration in the pharmaceutical industry. Different crystalline forms (polymorphs) of a drug molecule can present nonequivalent physicochemical properties and mechanical characteristics, due to varying factors such as crystal packing and molecular orientation, which can impact various physicochemical properties of the drug material, such as the hardness, hygroscopicity, solubility, stability, and pharmacokinetics. This aspect of polymorphism can have significant implications in pharmaceuticals, affecting for example the choice of excipients in a formulation, suitable routes of administration, dosage, the shelf-life, and also suitable methods for production and packaging. In cases when a drug molecule has more than one crystalline forms (i.e., different polymorphs), one polymorph may be better suited for a particular application, route of administration, or use than another polymorph of the same drug molecule.

Pitolisant hydrochloride is a drug molecule that is useful for treating various diseases and disorders, particularly sleep disorders such as excessive daytime sleepiness (EDS) and cataplexy, that is marketed as WAKIX®. WAKIX® contains a particular crystalline form of pitolisant hydrochloride, referred to herein as Form I, which has been disclosed in U.S. Pat. No. 8,207,197 that is incorporated herein by reference in its entirety.

SUMMARY

The present disclosure relates generally to a new crystalline form of pitolisant hydrochloride, hereinafter "Form II," and pharmaceutical compositions and dosage forms comprising Form II, as well as methods of treating a disease or disorder with Form II or a pharmaceutical composition or dosage form comprising Form II.

In some aspects, the present disclosure relates to a crystalline form of a compound represented by Formula (I):

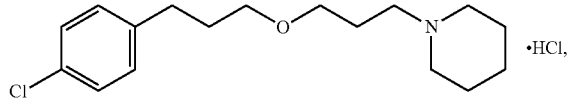

(I)

characterized by having an X-ray diffraction pattern comprising at least one of the following peaks, in terms of 2-theta (2θ), at 16.8°, 18.2°, 18.5°, 21.0°, and 25.1° (±) 0.2°. For example, the crystalline form may be characterized by having an X-ray diffraction pattern that comprises at least one of the characteristic peaks (2θ) at 15.8°, 16.8°, 18.2°, 18.5°, 18.8°, 19.3°, 20.1°, 21.1°, and 25.1° (±) 0.2°. Alternatively, the crystalline form may be characterized by having an X-ray diffraction pattern substantially as shown in pattern A of FIG. 1.

In an embodiment, the present disclosure relates to a crystalline form of a compound represented by Formula (I):

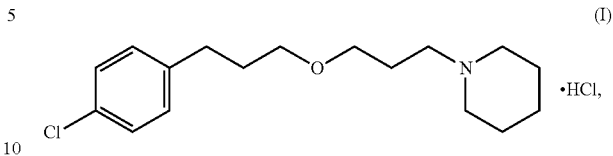

(I)

characterized by having an X-ray diffraction pattern comprising the following peaks, in terms of 2-theta (2θ), at 16.8°, 18.2°, 18.5°, 21.0°, and 25.1° (±) 0.2°. For example, the crystalline form may be characterized by having an X-ray diffraction pattern that comprises the characteristic peaks (2θ) at 15.8°, 16.8°, 18.2°, 18.5°, 18.8°, 19.3°, 20.1°, 21.1°, and 25.1° (±0.2°).

The XRPD pattern can be obtained using any suitable protocol and with any suitable apparatus, such as a protocol or apparatus disclosed herein. The XRPD pattern may be obtained using a sample of between about 1 mg and about 10 mg (e.g., between about 1 and about 5 mg, e.g., about 2 mg, about 3 mg, about 4 mg, or about 5 mg). The XRPD pattern may be obtained using Cu Kα radiation.

A crystalline form of the present disclosure may also be characterized by having an endothermic peak with an onset between about 90° C. and about 97° C., as obtained by differential scanning calorimetry (DSC). For example, the onset may be between about 91° C. and about 96° C., e.g., between about 92° C. and about 95° C., or between about 93° C. and about 94° C. The endothermic peak can be between about 92° C. and about 94° C. (e.g., about 92° C., about 93° C., or about 94° C.), or between about 95° C. and about 98° C. (e.g., about 95° C., about 96° C., or about 97° C.), as determined by DSC.

A crystalline form of the present disclosure may be characterized by DSC using a sample of between about 1 mg and about 10 mg (e.g., between about 1 and about 5 mg, e.g., about 2 mg, about 3 mg, about 4 mg, or about 5 mg). The DSC can be carried out under nitrogen. The DSC can be carried out at using a heating rate of 10° C./min. The DSC can be carried out at a temperature between 0° C. to 150° C., e.g., between 73° C. to 150° C.

In some aspects, a crystalline form of the present disclosure is characterized and/or formed using the following protocol: (i) heating from 20° C. to 150° C. at a rate of 10° C./min; (ii) cooling from 150° C. to 0° C. at a rate of 10° C./min; (iii) heating from 0° C. to 140° C. at a rate of 10° C./min; (iv) cooling from 140° C. to 0° C. at a rate of 200° C./min; (v) holding at 0° C. for 2 minutes; (vi) heating from 0° C. to 140° C. at a rate of 10° C./min; (vii) cooling from 140° C. to 73° C. at a rate of 10° C./min; (viii) holding at 73° C. for 4 minutes; and (ix) heating from 73° C. to 150° C. at a rate of 10° C./min.

In some aspects, a crystalline form of the present disclosure is characterized and/or formed using the following protocol: (i) heating from 20° C. to 130° C. at 10° C./min; (ii) cooling from 130° C. to 20° C. at 10° C./min; (iii) heating from 20° C. to 130° C. at 10° C./min; (iv) cooling from 130° C. to 72° C. at 10° C./min; (v) holding at 72° C. for 1 hour; and (vi) heating from 72° C. to 130° C. at 10° C./min.

In some embodiments, the present disclosure relates to a crystalline form of a compound represented by Formula (I):

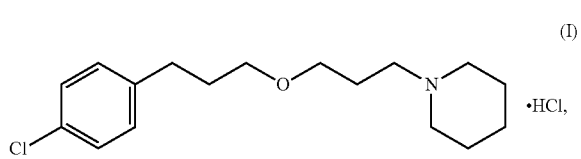 [SMILES: Clc1ccc(CCCOCCCN2CCCCC2)cc1]

characterized by having a melting point between about 90° C. and about 95° C. For example, the crystalline form can have a melting point between about 91° C. and about 94° C., e.g., between about 92° C. and about 94° C. In some aspects, the crystalline form has a melting point of about 93° C.

In some embodiments, the present disclosure relates to a crystalline form of a compound represented by Formula (I):

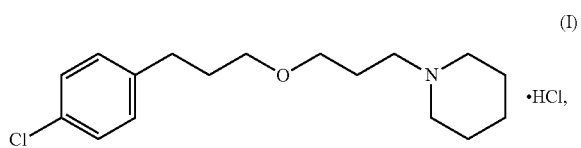 [SMILES: Clc1ccc(CCCOCCCN2CCCCC2)cc1]

characterized by having an endothermic peak with an onset between about 90° C. and about 97° C., as obtained by differential scanning calorimetry (DSC), e.g., an onset between about 91° C. and about 96° C., e.g., an onset between about 92° C. and about 95° C., or between about 93° C. and about 94° C. For example, the crystalline form may be characterized by having a DSC thermogram substantially as shown in FIG. 2, e.g., as shown in trace (7) of FIG. 2, e.g., as shown by peak (II) of FIG. 2. Alternatively, the crystalline form may be characterized by having a DSC thermogram substantially as shown in FIG. 3, e.g., as shown in trace (5) of FIG. 3, e.g., as shown by peak (II) of FIG. 3.

In some embodiments, the present disclosure relates to a crystalline form of a compound represented by Formula (I):

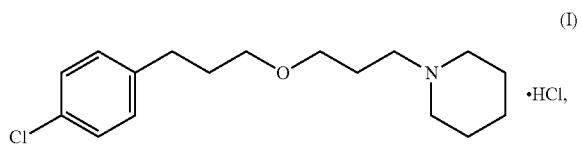 [SMILES: Clc1ccc(CCCOCCCN2CCCCC2)cc1]

characterized by having an X-ray diffraction pattern that does not comprise the combination of peaks (2θ) at 11.2°, 19.9°, 20.7°, and 34.1° (±) 0.2°. For example, a crystalline form of the present disclosure may be characterized by having an X-ray diffraction pattern that does not comprise the combination of peaks (2θ) at 11.2°, 15.4°, 16.3°, 16.9°, 17.8°, 19.9°, 20.7°, 21.0°, 21.8°, 22.6°, 24.5°, 24.6°, 25.0°, 25.5°, 26.3°, 28.3°, 30.3°, 34.1°, 35.8°, 40.0°, and 46.0° (±0.2°).

In some aspects, the present disclosure relates to a Form II polymorph of pitolisant hydrochloride.

In some aspects, the present disclosure relates to a pharmaceutical composition comprising a crystalline form or polymorph disclosed herein, and optionally a pharmaceutically acceptable excipient. The pharmaceutically acceptable excipient may be any suitable pharmaceutically acceptable excipient, such as a pharmaceutically acceptable excipient disclosed herein. In some embodiments, the pharmaceutically acceptable excipient is selected from the group consisting of colloidal silicon dioxide, crospovidone, magnesium stearate, microcrystalline cellulose, polyethylene glycol, polyvinyl alcohol, talc, and titanium dioxide. For example, the pharmaceutical composition may comprise a Form II polymorph of pitolisant hydrochloride.

In some aspects, the present disclosure relates to a dosage form comprising a crystalline form, polymorph, or pharmaceutical composition disclosed herein. The dosage form may be any suitable dosage form, such as a tablet, caplet, or capsule. For example, the dosage form may comprise a Form II polymorph of pitolisant hydrochloride.

In some embodiments, the present disclosure relates to a method of treating a disease or disorder, comprising administering to a subject in need thereof a crystalline form, polymorph, pharmaceutical composition, or dosage form disclosed herein. The disease or disorder may be a sleep disorder. For example, the disease or disorder may be excessive daytime sleepiness (EDS), cataplexy, narcolepsy, sleep apnea (e.g., obstructive sleep apnea), sleep induced apnea, or diurnal somnolence. In some embodiments, the disease or disorder is excessive daytime sleepiness (EDS). In some embodiments, the disease or disorder is cataplexy. In a method disclosed herein, the subject to be treated may have narcolepsy, and/or may be an adult with narcolepsy. For example, the method of treating a disease or disorder may comprise administering to a subject in need thereof a Form II polymorph of pitolisant hydrochloride.

In some aspects, the present disclosure relates to a crystalline form, polymorph, pharmaceutical composition, or dosage form disclosed herein, for use in the treatment of a disease or disorder (e.g., a disease or disorder disclosed herein), optionally, wherein the disease or disorder is excessive daytime sleepiness (EDS), cataplexy, narcolepsy, sleep apnea (e.g., obstructive sleep apnea), sleep induced apnea, or diurnal somnolence. The disease or disorder may be in a subject with narcolepsy (e.g., an adult subject with narcolepsy). In some aspects, the present disclosure relates to a Form II polymorph of pitolisant hydrochloride in the treatment of a disease or disorder (e.g., a disease or disorder disclosed herein), optionally, wherein the disease or disorder is excessive daytime sleepiness (EDS), cataplexy, narcolepsy, sleep apnea (e.g., obstructive sleep apnea), sleep induced apnea, or diurnal somnolence. The disease or disorder may be in a subject with narcolepsy (e.g., an adult subject with narcolepsy)

In some aspects, the present disclosure relates to the use of a crystalline form, polymorph, pharmaceutical composition, or dosage form disclosed herein, for the manufacture of a medicament for the treatment of a disease or disorder (e.g., a disease or disorder disclosed herein), optionally, wherein the disease or disorder is excessive daytime sleepiness (EDS), cataplexy, narcolepsy, sleep apnea (e.g., obstructive sleep apnea), sleep induced apnea, or diurnal somnolence. The disease or disorder can be in a subject with narcolepsy (e.g., an adult subject with narcolepsy). In some aspects, the present disclosure relates to the use of a Form II polymorph of pitolisant hydrochloride for the manufacture of a medicament for the treatment of a disease or disorder (e.g., a disease or disorder disclosed herein), optionally, wherein the disease or disorder is excessive daytime sleepiness (EDS), cataplexy, narcolepsy, sleep apnea (e.g., obstructive sleep apnea), sleep induced apnea, or diurnal somnolence. The disease or disorder can be in a subject with narcolepsy (e.g., an adult subject with narcolepsy).

In some aspects, the present disclosure relates to a crystalline form, polymorph, pharmaceutical composition, or dosage form of any one of claims for use in treating a disease or disorder in a subject in need thereof, such as a disease or disorder disclosed herein, e.g., a sleep disorder, excessive daytime sleepiness (EDS), cataplexy, narcolepsy, sleep apnea (e.g., obstructive sleep apnea), sleep induced apnea, or diurnal somnolence. For example, a Form II polymorph of pitolisant hydrochloride for use in treating a disease or disorder in a subject in need thereof, such as a disease or disorder disclosed herein, e.g., a sleep disorder, excessive daytime sleepiness (EDS), cataplexy, narcolepsy, sleep apnea (e.g., obstructive sleep apnea), sleep induced apnea, or diurnal somnolence. In some aspects, the disease or disorder is excessive daytime sleepiness (EDS). In some aspects, the disease or disorder is cataplexy. In some aspects, the subject has narcolepsy (e.g., the subject is an adult with narcolepsy).

DETAILED DESCRIPTION

Figure 1:
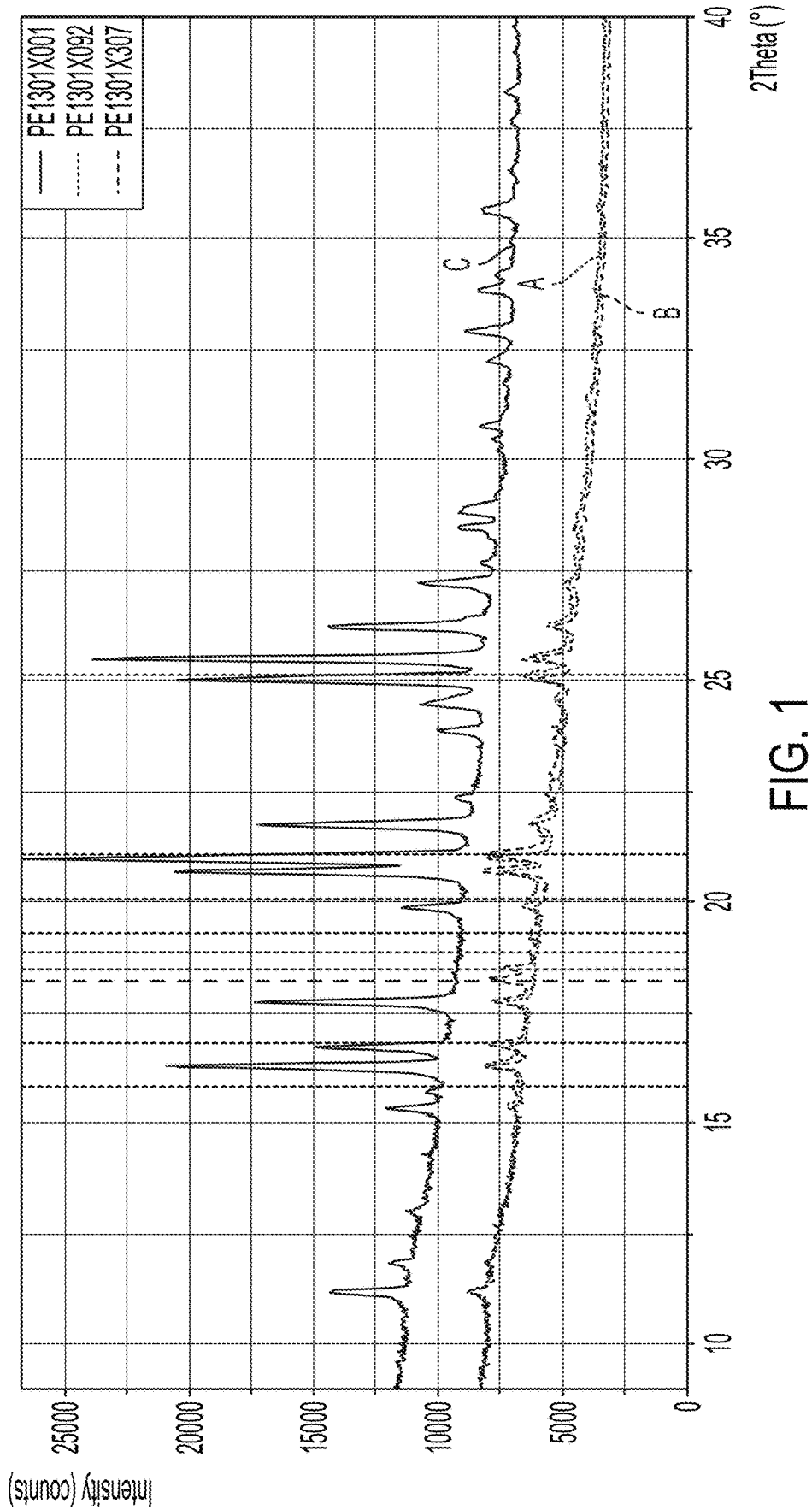
FIG. 1 is a graphical representation and overlay of X-ray powder diffraction (XRPD) patterns. The pattern in the middle of the overlay labeled "A" is the XRPD pattern obtained from a sample containing Form II crystals. The bottom pattern in the overlay labeled "B" shows the XRPD pattern obtained from the same sample after 10 months of storage. The pattern labeled "C" at the top of the overlay was obtained from pure Form I crystals. Vertical dashed lines highlight the characteristic peaks of Form II.

The present disclosure relates generally to a new crystalline form (polymorph) of pitolisant hydrochloride, which is referred to herein as "Form II." Also disclosed are pharmaceutical compositions and dosage forms comprising Form II and optionally a pharmaceutically acceptable excipient. Additionally, the present disclosure relates to methods of treating a disease or disorder using Form II, or a pharmaceutical composition or dosage form comprising Form II.

The structure of pitolisant hydrochloride (which may also be referred to herein as pitolisant monohydrochloride) is provided below as Formula (I):

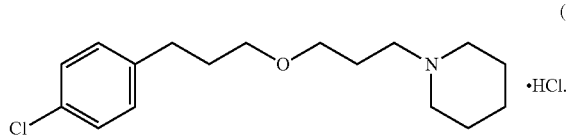

(I)

A crystalline form of pitolisant hydrochloride (Form I) was disclosed in U.S. Pat. No. 8,207,197, which is incorporated herein by reference in its entirety. The Form I polymorph is present in the FDA-approved pharmaceutical WAKIX®. The crystalline form of the present disclosure (i.e., Form II) is different than Form I. It is believed that Form II may have certain properties that are different than Form I, e.g., different degree of hygroscopicity, solubility, and/or pharmacokinetics, that may be advantageous for certain uses, e.g., in the treatment of a disease or disorder, such as EDS or cataplexy.

Definitions

The articles "a" and "an" are used herein to refer to one or more than one (i.e., to at least one) of the grammatical object of the article. By way of example, "an element" means one element or more than one element.

The term "about" when referring to a measurable value such as an amount, a temporal duration, and the like, is meant to encompass variations of ±20% or less, or in some instances ±15% or less, or in some instances ±10% or less, or in some instances ±5% or less, or in some instances ±1% or less, or in some instances ±0.1% or less, from the specified value, as such variations are appropriate.

The phrase "and/or" as used herein should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The terms "administer," "administering," or "administration," as used herein refer to implanting, absorbing, ingesting, injecting, inhaling, or otherwise introducing a compound (e.g., Form II), dosage form, or pharmaceutical composition.

The terms "comprise," "comprises," and "comprising" are used herein in a non-exclusive sense, except where the context requires otherwise. Likewise, the term "include" and its grammatical variants are intended to be non-limiting, such that recitation of items in a list is not to the exclusion of other like items that can be substituted or added to the listed items.

The term "effective amount" or a "therapeutically effective amount" as used herein refers to an amount of a compound, a dosage form, or a pharmaceutical composition, described herein, which is sufficient to achieve a desired result under the conditions of administration. For example, an effective amount of a compound, dosage form, or pharmaceutical composition disclosed herein for treating excessive sleep disorder (EDS), e.g., in a subject with narcolepsy, is an amount that can reduce the effects of the EDS, and/or reduce or eliminate the severity of a symptom associated with the EDS. A skilled clinician can determine appropriate dosing based on a variety of considerations including the severity of the disease, the subject's age, weight, general health and other considerations. A compound (e.g., a crystalline form, e.g., Form II), dosage form, or pharmaceutical composition disclosed herein may be administered to provide an amount of about 0.01 mg to about 250 mg (e.g., about 0.1 mg to about 100 mg) of a pharmaceutically active agent, e.g., about 1 mg, about 2 mg, about 3 mg, about 4 mg, about 5 mg, about 10 mg, about 15 mg, about 20 mg, about 30 mg, or about 40 mg.

The term "pharmaceutically acceptable excipient" as used herein refers to a non-toxic material that may be formulated with a compound disclosed herein (e.g., a crystalline form, e.g., Form II) to provide a pharmaceutical composition. Preferably, the pharmaceutically acceptable excipient is inert and does not interfere with the pharmacological activity of a compound which it is formulated with. Pharmaceutically acceptable excipients useful in the manufacture of the pharmaceutical compositions disclosed herein are any of those well known in the art, and include without limitation, diluents, dispersing agents, granulating agents, surface active agents, emulsifiers, disintegrating agents (sometimes referred to herein as disintegrants), binding agents (sometimes referred to herein as binders), preservatives, buffering agents (sometimes referred to herein as buffers), lubricating agents (sometimes referred to herein as lubricants), glidants, adjuvants, fillers, wetting agents, suspending agents, solvents, dispersion media, ion exchangers, salts, electrolytes, waxes, and/or oils, and the like.

For example, a pharmaceutically acceptable excipient may be alumina, a phosphate (e.g., calcium phosphate, dicalcium phosphate, tricalcium phosphate, disodium hydrogen phosphate, potassium hydrogen phosphate), a sulfate (e.g., calcium sulfate), a cellulose, kaolin, bentonite, lactose, mannitol, sorbitol, sucrose, inositol, compressible sugar, trehalose, xylitol, acacia, gelatin, glucose, maltodextrin, starch (e.g., corn starch, potato starch), sodium starch glycolate, starch derivatives, an amino acid, magnesium carbonate, polyvinylpyrrolidone (PVP, povidone) (e.g., cross-linked PVP, crospovidone), polyvinyl alcohol, tragacanth, polyethylene glycol, mineral clay powders, croscarmellose, poloxamer, fatty acids or salts thereof (e.g., lauric acid, sodium lauryl sulfate, stearic acid, calcium stearate, magnesium stearate, aluminum stearate, oleic acid), hydrogenated vegetable oils, talc, titanium dioxide, glyceryl behenate, silicon dioxide (e.g., colloidal silicon dioxide), a silicate salt (e.g., magnesium trisilicate), lecithin, serum protein (e.g., human serum albumin), sorbic acid, potassium sorbate, a metal cation salt (e.g., a sodium salt, such as sodium chloride, a potassium salt, such as potassium chloride, a magnesium salt, such as or magnesium chloride, a zinc salt, such as zinc chloride), water, dimethylacetamide, protamine sulfate, wool fat, ethylenediaminetetraacetic acid (EDTA), a cyclodextrin (e.g., CAPTISOL®), a polysorbate (e.g., TWEEN®, e.g., TWEEN® 20 or TWEEN® 80), and combinations thereof.

The term "pharmaceutically acceptable salt" as used herein refers to salts of a compound prepared with relatively nontoxic acids or bases, depending on the particular substituents found on the respective compound. When compounds contain relatively basic functionalities, acid addition salts can be obtained by contacting the neutral form of such compounds with a sufficient amount of the desired acid, either neat or in a suitable solvent (e.g., an inert solvent). Examples of pharmaceutically acceptable acid addition salts include those derived from inorganic acids like hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, or phosphorous acids and the like, as well as the salts derived from organic acids like acetic acid, propionic acid, isobutyric acid, maleic acid, malonic acid, benzoic acid, succinic acid, suberic acid, fumaric acid, lactic acid, mandelic acid, pamoic acid, phthalic acid, benzenesulfonic acid, p-toluenesulfonic acid, citric acid, tartaric acid, methanesulfonic acid, oxalic acid, and the like. Also included are salts of amino acids such as arginate and the like, and salts of organic acids like glucuronic or galacturonic acids and the like. Other pharmaceutically acceptable salts known to those of skill in the art are suitable for pharmaceutical compositions relating to the present disclosure.

The term "solvate" as used herein refers to forms of a compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. Compounds of the present disclosure may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" as used herein refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot xH_2O$, wherein R is the compound and wherein x is a number greater than 0. A given compound may form more than one type of hydrate, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "subject" as used herein refers to any animal, such as any mammal, including but not limited to, humans, non-human primates, rodents, dogs, and the like. Non-human primates include chimpanzees, cynomolgus monkeys, spider monkeys, and macaques (e.g., Rhesus). Rodents include mice, rats, woodchucks, ferrets, rabbits, and hamsters. Domestic and game animals include cows, horses, pigs, deer, bison, buffalo, feline species (e.g., domestic cat), canine species (e.g., dog, fox, wolf), avian species, and fish. In some embodiments, the subject is a mammal (e.g., a human, a rat, or a mouse). The subject can be male or female. The subject may be of any age, including an elderly human subject (e.g., 65 years or older), a human subject that is not elderly (e.g., less than 65 years old), or a human pediatric subject (e.g., less than 18 years old). In preferred aspects, the subject is a human.

As used herein, the terms "treat," "treatment," "treating," or grammatically related terms, refer to a method of reducing the effects of a disease or disorder. As is readily appreciated in the art, full eradication of the disease, disorder, or symptoms thereof is preferred but not a requirement for treatment. Desirable effects of treatment include, but are not limited to, preventing occurrence or recurrence of the disease or disorder, alleviation of symptoms, diminishment of any direct or indirect pathological consequences of the disease or disorder, or other improvement of any sign, symptom, or consequence of the disease or disorder, such as prolonged survival, less morbidity, and/or a lessening of side effects.

Throughout this disclosure, various embodiments can be presented in a range format (e.g., from X to Y). It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range. For example, description of a range, such as from 1 to 6, should be considered to have specifically disclosed subranges such as from 1 to 5, from 1 to 4, from 1 to 3, from 2 to 6, from 2 to 4, from 3 to 6, etc., as well as individual numbers within that range, e.g., 1, 2, 2.8, 3, 3.6, 4, 5, 5.4, and 6. As another example, a range such as 95-99% includes 95%, 96%, 97%, 98%, or 99% and all subranges such as 96-99%, 96-98%, 96-97%, 97-99%, 97-98%, etc. This applies regardless of the breadth of the range All publications (e.g., scientific journal articles, patent publications, and the like) cited in this disclosure are incorporated by reference in their entirety. To the extent the material incorporated by reference contradicts or is inconsistent with this specification, the specification will supersede any such material. The citation of any references herein is not an admission that such references are prior art to the present disclosure. Various terms relating to aspects of the description are used throughout the specification and claims. Such terms are to be given their ordinary meaning in the art unless otherwise indicated. Other specifically defined terms are to be construed in a manner consistent with the definitions provided herein.

Compounds (e.g., pharmaceutically active agents) disclosed herein may also comprise one or more isotopic substitutions. For example, hydrogen (H) may be in any isotopic form, including $^1$H, $^2$H (D or deuterium), $^3$H (T or tritium); carbon (C) may be in any isotopic form, including $^{12}$C, $^{13}$C, and $^{14}$C; oxygen (O) may be in any isotopic form, including $^{16}$O and $^{18}$O; nitrogen (N) may be in any isotopic form, including $^{14}$N and $^{15}$N; and chlorine (Cl) may be in any isotopic form, including $^{35}$Cl and $^{37}$Cl.

Various embodiments of the compounds, dosage forms, pharmaceutical compositions, and methods herein are described in further detail below, and additional definitions may be provided throughout the specification.

Crystalline Form of Pitolisant Hydrochloride

Disclosed herein is a crystalline form of pitolisant hydrochloride (Form II) (a Form II polymorph of pitolisant hydrochloride). Pitolisant hydrochloride is also known as 1-[3-[3-(4-chlorophenyl) propoxy]propyl]-piperidine monohydrochloride. Pitolisant hydrochloride is represented by Formula (I):

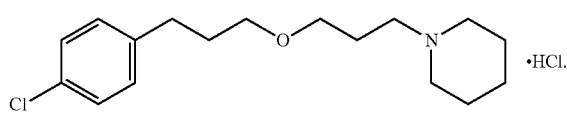

(I)

A crystalline form of pitolisant hydrochloride (Form I) was previously disclosed in U.S. Pat. No. 8,207,197, which is incorporated herein by reference in its entirety. This disclosure relates to another crystalline form, Form II, the preparation or characterization of which has not previously been disclosed. It will be understood that polymorphs disclosed herein are crystalline, i.e., not amorphous.

Form II can be characterized, and/or distinguished from Form I, using a suitable analytical technique such as X-ray powder diffraction (XRPD) or differential scanning calorimetry (DSC).

For example, Form II can be characterized using XRPD, as illustrated in Example 3 and FIG. 1. Similarly, XRPD can be used to distinguish Form I and Form II, which is also illustrated in FIG. 1 (e.g., comparing pattern A in the middle of the overlay, corresponding to sample containing Form II, to reference pattern C at the top of the overlay, which is the XRPD pattern of pure Form I crystals).

Form II may be characterized based by an XRPD pattern comprising one or more, or all of the following peaks, in terms of 2-theta (2θ): 16.8°, 18.2°, 18.5°, 21.0°, and 25.1°±0.2°. For example, Form II can be characterized based on an XRPD pattern comprising one or more, or all of, the following peaks (2θ) at 15.8°, 16.8°, 18.2°, 18.5°, 18.8°, 19.3°, 20.1°, 21.1°, and 25.1°±0.2°. Form II may be characterized based by an XRPD pattern comprising one or more, or all of the following peaks, in terms of 2-theta (2θ): 16.8°, 18.2°, 18.5°, 21.0°, and 25.1°±0.1°. For example, Form II can be characterized based on an XRPD pattern comprising one or more, or all of, the following peaks (2θ) at 15.8°, 16.8°, 18.2°, 18.5°, 18.8°, 19.3°, 20.1°, 21.1°, and 25.1° ±0.1°. Form II may be characterized based by an XRPD pattern comprising one or more, or all of the following peaks, in terms of 2-theta (2θ): 16.8°, 18.2°, 18.5°, 21.0°, and 25.1°±0.05°. For example, Form II can be characterized based on an XRPD pattern comprising one or more, or all of, the following peaks (2θ) at 15.8°, 16.8°, 18.2°, 18.5°, 18.8°, 19.3°, 20.1°, 21.1°, and 25.1°±0.05°. Form II may be characterized based by an XRPD pattern comprising one or more, or all of the following peaks, in terms of 2-theta (2θ): 16.8°, 18.2°, 18.5°, 21.0°, and 25.1°±0.02°. For example, Form II can be characterized based on an XRPD pattern comprising one or more, or all of, the following peaks (2θ) at 15.8°, 16.8°, 18.2°, 18.5°, 18.8°, 19.3°, 20.1°, 21.1°, and 25.1°±0.02°. Form II may be characterized based by an XRPD pattern comprising one or more, or all of the following peaks, in terms of 2-theta (2θ): 16.8°, 18.2°, 18.5°, 21.0°, and 25.1°. For example, Form II can be characterized based on an XRPD pattern comprising one or more, or all of, the following peaks (2θ) at 15.8°, 16.8°, 18.2°, 18.5°, 18.8°, 19.3°, 20.1°, 21.1°, and 25.1°. Form II may be characterized by having an XRPD pattern substantially as shown in pattern A of FIG. 1.

Form II may also be characterized, or differentiated from Form I, by the absence of peaks (2θ) in an XRPD pattern at one, or more, or all of 11.2°, 19.9°, 20.7°, and 34.1° (±) 0.2°. For example, Form II may be characterized, or differentiated from Form I, by the absence of peaks (2θ) in an XRPD pattern at one, or more, or all of 11.2°, 15.4°, 16.3°, 16.9°, 17.8°, 19.9°, 20.7°, 21.0°, 21.8°, 22.6°, 24.5°, 24.6°, 25.0°, 25.5°, 26.3°, 28.3°, 30.3°, 34.1°, 35.8°, 40.0°, and 46.0° (±0.2°).

The XRPD used to characterize Form II, and/or differentiate Form I and Form II, may be any suitable XRPD technique. For example, an XRPD pattern or peak disclosed herein can be acquired using Cu Kα radiation. For example, an XPRD technique disclosed herein can be used (see, e.g., Materials and Methods).

Figure 2:
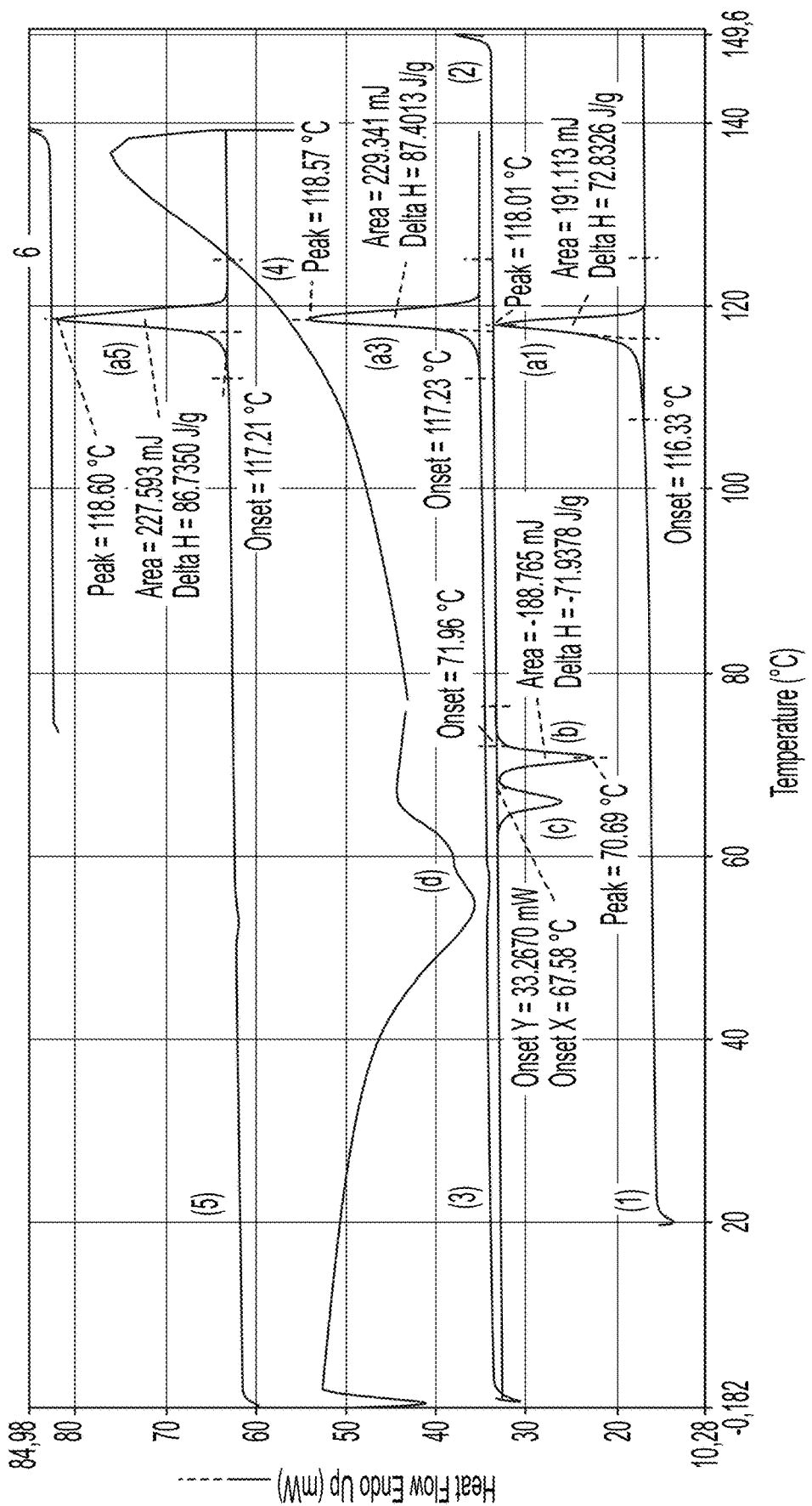
FIG. 2 shows a differential scanning calorimetry (DSC) thermogram following an exemplary protocol for obtaining Form II of pitolisant hydrochloride. The endothermic peak attributed to Form II is peak (II) in trace (7).
Figure 2:
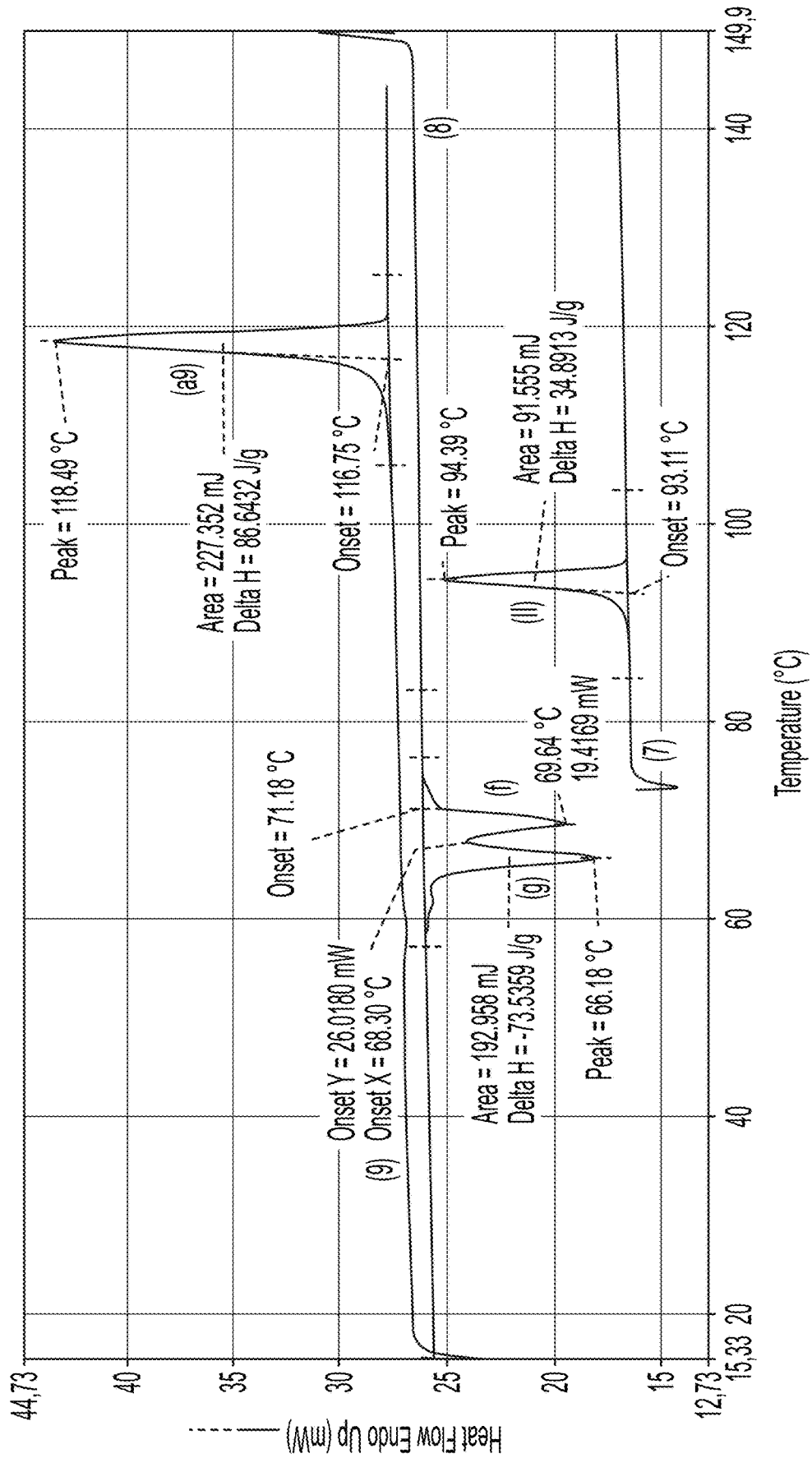
Figure 3:
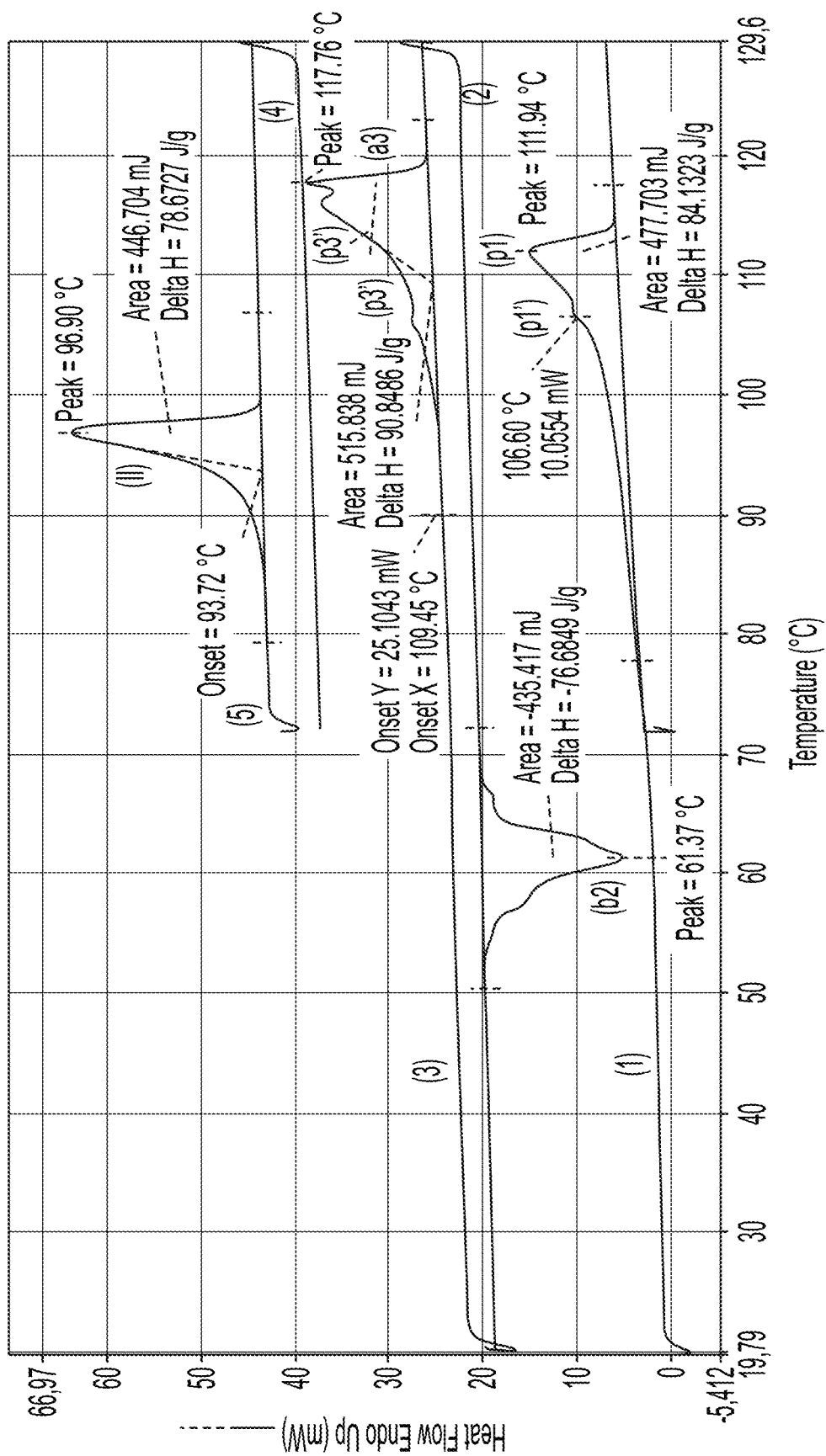
FIG. 3 shows another DSC thermogram following an exemplary protocol for obtaining Form II. The endothermic peak attributed to Form II is peak (II) in trace (5).
Figure 3:
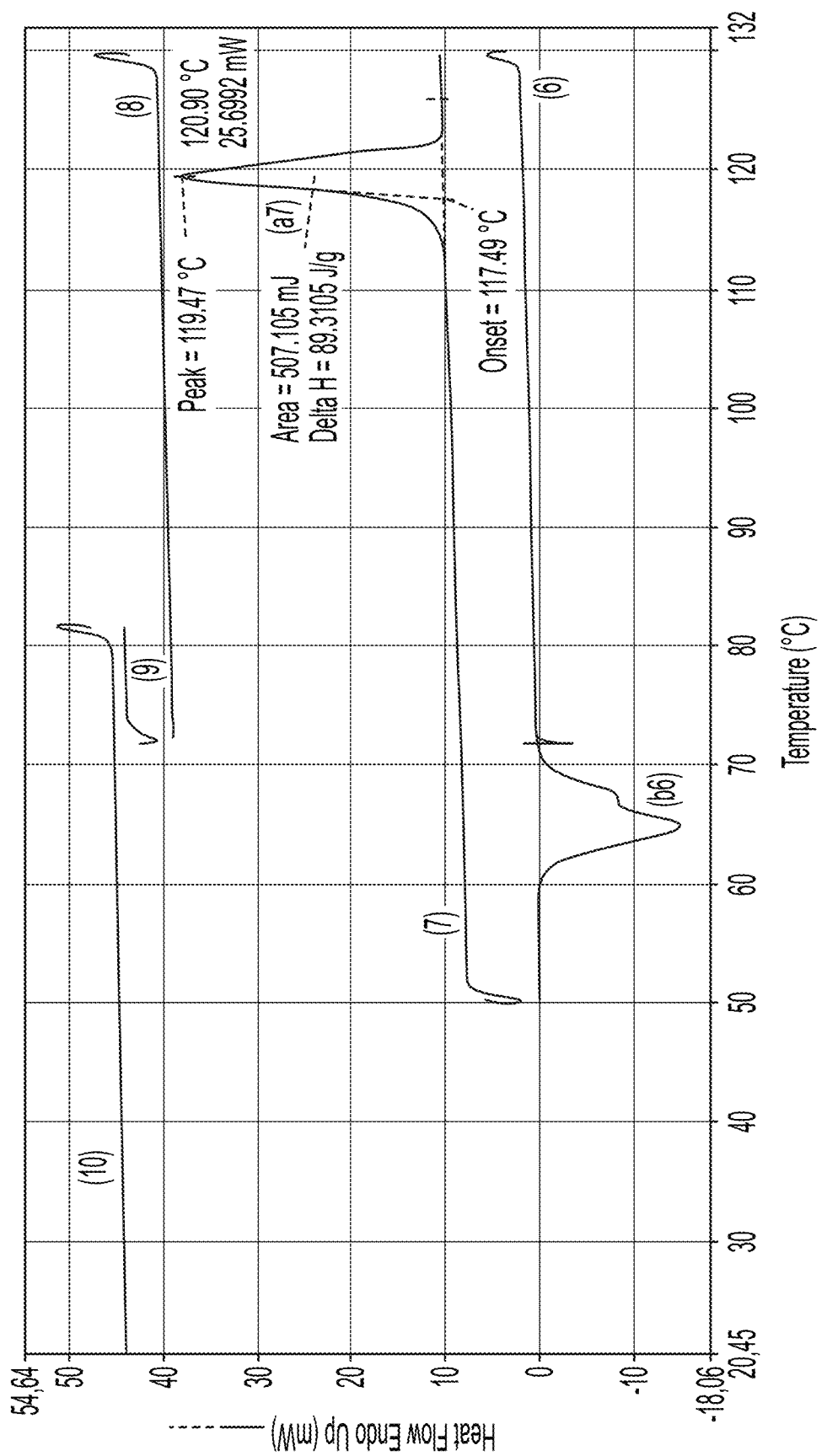

Form II can also be characterized using DSC, and/or distinguished from Form I using DSC, as illustrated in Example 2 and FIGS. 2 and 3.

For example, Form II may be characterized by having an endothermic peak with an onset between about 90° C. and about 97° C., as obtained by DSC. The endothermic peak of Form II may have an onset between about 91° C. and about 96° C., e.g., between about 92° C. and about 95° C., or between about 93° C. and about 94° C. For example, Form II may be characterized by having an endothermic peak with an onset between 90° C. and 97° C., as obtained by DSC. The endothermic peak of Form II may have an onset between 91° C. and 96° C., e.g., between 92° C. and 95° C., or between 93° C. and 94° C.

In contrast, Form I may be characterized by having an endothermic peak with an onset between about 115° C. and about 119° C., as obtained by DSC, e.g., between about 116° C. and about 118° C., e.g., about 117° C. Form I may be characterized by having an endothermic peak with an onset between 115° C. and 119° C., as obtained by DSC, e.g., between 116° C. and 118° C., e.g., 117° C.

As such, Form II may be characterized by having an endothermic peak with an onset that is lower than the onset of an endothermic peak attributed to Form I, as obtained by DSC. For example, Form II may have an endothermic peak with an onset between about 20° C. and about 30° C. lower than the onset of an endothermic peak associated with Form I, e.g., between about 22° C. and about 18° C. lower, e.g., about 23° C. lower, about 24° C. lower, or about 25° C. lower.

Alternatively, Form II may be characterized by having an endothermic peak at a temperature between about 92° C. and about 94° C., as determined by DSC, e.g., about 92° C., about 93° C., or about 94° C. Alternatively, Form II may be characterized by having an endothermic peak at a temperature between about 95° C. and about 98° C., as determined by DSC, e.g., about 95° C., about 96° C., or about 97° C. For example, Form II may be characterized by having an endothermic peak at a temperature between 92° C. and 94° C., as determined by DSC, e.g., 92° C., 93° C., or 94° C. Alternatively, Form II may be characterized by having an endothermic peak at a temperature between 95° C. and 98° C., as determined by DSC, e.g., 95° C., 96° C., or 97° C.

In contrast, Form I may be characterized by having an endothermic peak at a temperature between about 116° C. and about 120° C., as determined by DSC, e.g., about 117° C., about 118° C., or about 119° C. For example, Form I may be characterized by having an endothermic peak at a temperature between 116° C. and 120° C., as determined by DSC, e.g., 117° C., 118° C., or 119° C.

Form II may be characterized by having a melting point between about 90° C. and about 95° C., as determined by any suitable technique (e.g., closed capillary tube, or DSC). For example, Form II may be characterized by having a melting point between 90° C. and 95° C. For example, Form II may be characterized by having a melting point between about 91° C. and about 94° C., e.g., between about 92° C. and about 94° C. For example, Form II may be characterized by having a melting point between 91° C. and 94° C., e.g., between 92° C. and 94° C. Form II may be characterized by having a melting point of about 93° C. Form II may be characterized by having a melting point of 93° C.

In contrast, Form I can be characterized by having a higher melting point than Form II. The melting point of Form I is about 117° C. As such, Form II may be identified by having a melting point about 20° C. to about 30° C. lower than the melting point of Form I, e.g., between about 22° C. and about 18° C. lower, e.g., about 23° C. lower, about 24° C. lower, or about 25° C. lower.

In addition to being used to identify an endothermic peak and/or melting point of a polymorph, DSC may also be used to obtain Form II (e.g., from a sample of pitolisant hydrochloride, e.g., from Form I). For example, DSC can be used to convert pitolisant hydrochloride that is substantially Form I into pitolisant hydrochloride that is substantially Form II.

The DSC protocol used to determine an endothermic peak, a melting point, or to obtain Form II, as disclosed herein, may be any suitable DSC protocol, such as a DSC protocol disclosed herein, e.g., Protocol 1 or Protocol 2 described in Example 2. For example, the DSC can be carried out using a sample of a few milligrams of pitolisant hydrochloride, e.g., between about 1 mg and about 10 mg, e.g., between about 1 and about 5 mg, e.g., about 2 mg, about 3 mg, about 4 mg, or about 5 mg. For example, the DSC can be carried out using between 1 mg and 10 mg of pitolisant hydrochloride, e.g., between 1 and 5 mg, e.g., 2 mg, 3 mg, 4 mg, or 5 mg. The DSC may be carried out under nitrogen. The DSC may carried out at a heating rate of about 10° C./min. The DSC may be carried out within a temperature range between about 0° C. and about 150° C., e.g., between about 73° C. and about 150° C.

For example, the DSC used to determine an endothermic peak or melting point disclosed herein, or to obtain Form II, can be carried out with one or more, or all of, the following steps: (i) heating from about 20° C. to about 150° C. at a rate of about 10° C./min; (ii) cooling from about 150° C. to about 0° C. at a rate of 10° C./min; (iii) heating from about 0° C. to about 140° C. at a rate of about 10° C./min; (iv) cooling from about 140° C. to about 0° C. at a rate of about 200° C./min; (v) holding at about 0° C. for about 2 minutes; (vi) heating from about 0° C. to about 140° C. at a rate of about 10° C./min; (vii) cooling from about 140° C. to about 73° C. at a rate of 10° C./min; (viii) holding at about 73° C. for about 4 minutes; and (ix) heating from about 73° C. to about 150° C. at a rate of about 10° C./min.

For example, the DSC used to determine an endothermic peak or melting point disclosed herein, or to obtain Form II, can be carried out with one or more, or all of, the following steps: (i) heating from 20° C. to 150° C. at a rate of 10° C./min; (ii) cooling from 150° C. to 0° C. at a rate of 10° C./min; (iii) heating from 0° C. to 140° C. at a rate of 10° C./min; (iv) cooling from 140° C. to 0° C. at a rate of 200° C./min; (v) holding at 0° C. for 2 minutes; (vi) heating from 0° C. to 140° C. at a rate of 10° C./min; (vii) cooling from 140° C. to 73° C. at a rate of 10° C./min; (viii) holding at 73° C. for 4 minutes; and (ix) heating from 73° C. to 150° C. at a rate of 10° C./min.

Alternatively, the DSC used to determine an endothermic peak or melting point disclosed herein, or to obtain Form II, can be carried out with one or more, or all of, the following steps: (i) heating from about 20° C. to about 130° C. at about 10° C./min; (ii) cooling from about 130° C. to about 20° C. at about 10° C./min; (iii) heating from about 20° C. to about 130° C. at about 10° C./min; (iv) cooling from about 130° C. to about 72° C. at about 10° C./min; (v) holding at about 72° C. for about 1 hour; and (vi) heating from about 72° C. to about 130° C. at about 10° C./min.

For example, the DSC used to determine an endothermic peak or melting point disclosed herein, or to obtain Form II, can be carried out with one or more, or all of, the following steps: (i) heating from 20° C. to 130° C. at 10° C./min; (ii) cooling from 130° C. to 20° C. at 10° C./min; (iii) heating from 20° C. to 130° C. at 10° C./min; (iv) cooling from 130° C. to 72° C. at 10° C./min; (v) holding at 72° C. for 1 hour; and (vi) heating from 72° C. to 130° C. at 10° C./min.

Form II may be characterized by having a (DSC) thermogram substantially as shown in FIG. 2. For example, Form II may be characterized by having a DSC thermogram substantially as shown in trace (7) of FIG. 2, and/or by having an endothermic peak substantially as shown by peak (II) of FIG. 2.

Alternatively, Form II may be characterized by having a (DSC) thermogram substantially as shown in FIG. 3. For example, Form II may be characterized by having a DSC thermogram substantially as shown in trace (5) of FIG. 3, and/or by having an endothermic peak substantially as shown by peak (II) of FIG. 3.

Dosage Forms and Pharmaceutical Compositions

Disclosed herein are dosage forms and pharmaceutical compositions comprising Form II, and optionally one or more pharmaceutically acceptable excipients.

The dosage form or pharmaceutical composition can comprise a therapeutically effective amount of Form II. For example, the dosage form or pharmaceutical composition may comprise between about 1 mg and about 200 mg of Form II, e.g., between about 1 mg and about 100 mg, between about 1 mg and about 50 mg, between about 10 mg and about 25 mg, or between about 1 mg and about 10 mg, of Form II, e.g., about 3 mg, about 4 mg, about 5 mg, about 6 mg, about 8 mg, about 10 mg, about 12 mg, about 15 mg, about 20 mg, about 25 mg, about 30 mg, about 40 mg, or about 50 mg, of Form II.

It will be understood that because Form II comprises a pharmaceutically acceptable salt of pitolisant, the amount of pharmaceutically active agent in the dosage form or pharmaceutical composition will be slightly higher than the equivalent amount of free base. For example, a dosage form or pharmaceutical composition disclosed herein comprising 5 mg of pitolisant hydrochloride (as Form II) will comprise about 4.45 mg of pitolisant (freebase). In another example, a dosage form or pharmaceutical composition disclosed herein comprising 20 mg of pitolisant hydrochloride comprises about 17.8 mg of pitolisant (freebase). In some embodiments, a dosage form or pharmaceutical composition disclosed herein comprises about 5 mg of pitolisant monohydrochloride, or about 4.45 mg pitolisant (freebase). In some embodiments, a dosage form or pharmaceutical composition disclosed herein comprises about 20 mg of pitolisant monohydrochloride, or about 17.8 mg pitolisant (freebase).

The dosage forms of the present disclosure can be tablets, caplets, capsules, suspensions, granules, powders, or the like.

The dosage forms or pharmaceutical compositions of the present disclosure can further comprise one or more pharmaceutically acceptable excipients, such as diluents, dispersing agents, granulating agents, surface active agents, emulsifiers, disintegrating agents (sometimes referred to herein as disintegrants), binding agents (sometimes referred to herein as binders), preservatives, buffering agents, lubricating agents (sometimes referred to herein as lubricants), glidants, adjuvants, fillers, wetting agents, suspending agents, solvents, dispersion media, ion exchangers, salts, electrolytes, waxes, and/or oils, and the like. The pharmaceutical composition or dosage form may comprise a pharmaceutically acceptable disclosed herein, or a combination of pharmaceutically acceptable excipients disclosed herein. For example, a dosage form or pharmaceutical composition of the present disclosure may comprise one or more, or all of, the following pharmaceutically acceptable excipients: colloidal silicon dioxide, crospovidone, magnesium stearate, microcrystalline cellulose, polyethylene glycol, polyvinyl alcohol, talc, and titanium dioxide.

Each pharmaceutically acceptable excipient can be present in the dosage form or pharmaceutical composition in any suitable amount. For example, a pharmaceutically acceptable excipient can be present in the dosage form or pharmaceutical composition in an amount of between about 0.01% and about 95% by weight of the dosage form or pharmaceutical composition, e.g., between about 0.1% and about 25%, between about 1% and about 10%, between about 15% and about 95% and about 0.01% and about 2%, by weight of the dosage form or pharmaceutical composition.

Dosage forms and pharmaceutical compositions of the present disclosure may be administered orally, parenterally, by inhalation, topically, rectally, nasally, buccally, vaginally, or by implantation.

Preparation of the dosage forms or pharmaceutical composition of the present disclosure can include conventional methods, such as blending, filling, compressing (e.g., direct compression, compression of dry, wet or sintered granules), coating (e.g., coating in a spray process), extrusion, granulation (e.g., wet or dry granulation), pelleting (e.g., direct pelleting), binding, powder layering (e.g., onto active ingredient-free beads, or neutral cores or particles of pharmaceutically active agent), and rounding off.

Methods of Treatment

The present disclosure further relates to a method for the treatment of a disease or disorder, comprising administering Form II, or a dosage form or pharmaceutical composition disclosed herein, to a subject in need thereof. The disease or disorder may be a sleep disorder (e.g., excessive daytime sleepiness (EDS), cataplexy, narcolepsy, sleep apnea (e.g., obstructive sleep apnea), sleep induced apnea, diurnal somnolence), central nervous system disorder (e.g., epilepsy, Alzheimer's disease, Parkinson's disease, dementia (e.g., dementia with Lewy bodies and/or vascular dementia), attention disorders, wakefulness disorders, memorization disorders, cognitive deficits (e.g., in aged persons), psychiatric pathologies, depressive and asthenic states, vertigo, and motion sickness), obesity, psychosomatic disorders, respiratory disorders, allergic conditions, inflammatory conditions, cardiac conditions, gastrointestinal conditions, conditions of the urogenital system, conditions of the cutaneous system, stress, migraine, headache, pain, psychotropic disorders, asthma, bronchitis, rhinitis, tracheitis, gastric ulcers, duodenal ulcers, ulcerative colitis, Crohn's disease, irritable bowel syndrome (IBS), cystitis, metritis, urinary incontinence, fecal incontinence, urticaria, itching, arthritis, conjunctivitis, premenstrual syndrome, prostatic inflammations, genital disorders, rheumatic conditions, ocular conditions, sialorrhea, convulsion, depression, disorders of the hypothalamusophyseal system, disorders of the cerebral circulation, and disorders of the immune system.

In preferred aspects, the disease or disorder is a sleep disorder. For example, the disease or disorder can be excessive daytime sleepiness (EDS). The EDS can be in subjects (e.g., adult subjects) with narcolepsy.

The present disclosure further relates to a method for the prevention of undesirable side effects associated with using antipsychotic or antidepressant agents (e.g., aripiprazole, clozapine, olanzapine, risperidone, quetiapine, sertindole, mirtazapine, amitryptyline, and paroxetine), comprising administering Form II, or a dosage form or pharmaceutical composition of the present disclosure, to a subject in need thereof. Non-limiting examples of undesirable side effects associated with using antipsychotic or antidepressant agents includes weight gain, somnolence, and cognitive impairment.

The present disclosure further relates to a method for (i) inducing an extended state of wakefulness; (ii) improving cognitive processes; (iii) reducing food intake; and/or (iv) normalizing vestibular reflexes, comprising administering Form II, or a dosage form or pharmaceutical composition disclosed herein, to a subject in need thereof.

Form II, or a dosage form or pharmaceutical composition disclosed herein, may be administered once daily, twice daily, or more often. More than one dosage form can be administered at once to achieve a desired dose. Form II, or a dosage form or pharmaceutical composition disclosed herein, may be taken with a frequency and in such an amount so that the total amount of pitolisant (in terms of freebase) administered is within the range of from about 10 mg to about 50 mg per day, e.g., about 15 mg to about 40 mg per day. Form II, or a dosage form or pharmaceutical compositions disclosed herein, may be taken with a frequency and in such an amount so that the total amount of pitolisant (in terms of freebase) administered is within the range of from about 17.8 mg to about 35.6 mg per day. For example, a subject may be administered orally two dosage forms once daily, where each dosage form comprises 4.45 mg pitolisant (in terms of freebase), to achieve a daily dose of 8.9 mg pitolisant (in terms of freebase). A subject may be administered orally one dosage form once daily, where the dosage form comprises 17.8 mg pitolisant (in terms of freebase), to achieve a daily dose of 17.8 mg pitolisant (in terms of freebase). A subject may be administered orally two dosage forms once daily, where each dosage form comprises 17.8 mg pitolisant (in terms of freebase), to achieve a daily dose of 35.6 mg pitolisant (free base).

EXAMPLES

Materials and Methods

General Method for Differential Scanning calorimetry (DSC): A few milligrams of sample was introduced into a 25 µL aluminium crucible and covered with a holed lid. DSC analyses were carried out under a nitrogen flush (20 mL/min), with temperature scans at 10° C./min, being adjusted according to experimental needs.

General Method for X-Ray Powder Diffraction (XRPD): Analyses in XRPD were carried out in transmission mode unless stated otherwise. A few milligrams of sample was wrapped in Kapton® foil (which exhibits a peak at (2θ)) 5.5°. Analyses were performed from (2θ) 2° to 50°.

TABLE 1

Characteristics of XRPD analysis.

Sample Mode: Transmission

| | |
|---|---|
| Measurement | Scan axis: Gonio |
| | Scan range (°): 3.0040-29.999 or 1.9960-50.0003 |
| | Step size (°): 0.0263 |
| | Measurement type: repeated scan (20 times) |
| | Sample offsets: Omega (°): 0.000 |
| | Sample movement: Movement type: Spinning |
| | Rotation time(s): 2.0 |
| Used wavelength | Intended wavelength type: Kα1 |
| | Kα1 (Å): 1.540598 |
| | Kα2 (Å): 1.544426 |
| | Kα2/Kα1 intensity ratio: 0.50 |
| | Kα (Å): 1.541874 |
| | Kβ (Å): 1.392250 |
| Incident Beam Path: Radius (mm): 240.0 | |
| X-ray tube | Name: PW3373/10 Cu LFF DK174558 |
| | Anode Material: Cu |
| | Voltage (kV): 40 |
| | Current (mA): 40 |
| | Focus type: Line (length (mm): 12.0 width (mm): 0.4 Take-off angle (°): 4.4) |
| X-ray mirror | Name: Inc. Beam Cu W/Si (parabolic MPD) Crystal (W/Si Graded Parabolic) |
| | Acceptance angle (°): 0.8 |
| | Length (mm): 55.3 |
| Slits | Soller slit: Soller 0.04 rad. Opening (rad.): 0.04 |
| | Anti-scatter slit: AS Slit 1.4 mm (mirror) Type: Fixed |
| | Height (mm): 1.40 |
| | Divergence slit: slit fixed ⅛° Distance to sample (mm): 140 Type: Fixed |
| | Height (mm): 0.19 Angle (°): 0.1089 |
| Diffracted Beam Path: Radius (mm): 240.0 | |
| Soller slit | Large soller 0.04 rad. Opening (rad.): 0.04 |
| Detector | Name: PIXcel Type: RTMS detector PHD-Lower level (%): 25.5 |
| | PHD-Upper Level (%): 70.0 Mode: Scanning |
| | Active length (°): 3.347 |
| Instrument/Software | |

Instrument ID: 0000000011026833
Application SW: X'Pert Data Collector vs. 2.2j
Instrument control SW: XPERT-PRO vs. 2.1D

Example 1. Synthesis of Pitolisant Monohydrochloride Crystals

Pitolisant monohydrochloride can be prepared according to methods described in U.S. Pat. No. 8,207,197, e.g., following the protocol provided below.

Sodium 3-piperidinopropanolate (2.13 kg; 12.88 mol), 3-(4-chlorophenyl) propyl mesylate (1.12 kg; 4.51 mol), and 0.322 mol of 15-crown-5 in dry toluene (4.5 kg) were refluxed for 4 hours. The solvent was evaporated and the residue purified by column chromatography on silica gel (eluent: methylene chloride/methanol, 9:1). The obtained oil was distilled in fractionating equipment at reduced pressure (0.3-0.7 mmHg) and with a heating jacket at 207-210° C. The head fractions and the distilled fraction were collected at 0.001-0.010 mmHg with a jacket temperature of 180-200° C., to provide pitolisant freebase (1-[3-[3-(4-chlorophenyl) propoxy]propyl]-piperidine) as an oil (1.0 kg; 3.38 mol).

Distilled 1-[3-[3-(4-chlorophenyl) propoxy]propyl]-piperidine (1.0 kg) and anhydrous ethyl acetate (4.5 kg) were transferred to a 10-L glass vessel fitted with a cooling bath and a gas inlet. A stream of gaseous hydrogen chloride was bubbled in the reaction mixture at 20-25° C. The pH of the solution was checked by taking a 0.5 mL sample of the reaction mixture and diluting it with 5 mL of deionized water, to obtain a pH of about 3-4.

The mixture was cooled to between −10° C. and −12° C. and stirred for 1 h. The precipitate was filtered by using a sintered glass filter and washed with 0.5 L of anhydrous ethyl acetate cooled to 0-5° C. The product was dried in a vacuum oven at 50° C. for a minimum period of 12 hours, to provide crude pitolisant monohydrochloride (1-[3-[3-(4-chlorophenyl) propoxy]propyl]-piperidine monohydrochloride) (1.10 kg).

A mixture of the crude pitolisant monohydrochloride, anhydrous ethyl acetate (3.98 kg) and isopropanol (0.35 kg) were heated slowly at 55-60° C. in a 10-L glass vessel fitted with a heating and cooling system, and the resulting solution was filtered through a heat-isolated sintered glass filter, keeping the temperature at 55-60° C. The solution was transferred to a 10 L glass vessel and the mass was slowly cooled to 0-5° C. for about 1 hour. The mixture was stirred at this temperature for 1 hour and the precipitate was filtered through a sintered glass filter. The solid was washed with a mixture of anhydrous ethyl acetate (1.6 kg) and isopropanol (0.14 kg) cooled at 0-5° C. The solid was dried in a vacuum oven at 50° C. for a minimum period of 12 hours to provide pure pitolisant monohydrochloride (1-[3-[3-(4-chlorophenyl) propoxy]propyl]-piperidine monohydrochloride) (M.p. 117-119° C.; yield 80%; IR spectrum (KBr): bands at 1112 and 1101 (C—O Ether/St. asym), 2936 and 2868 (Alkane CH(CH$_2$)/St.), 1455 (Alkane CH(CH$_2$)/Deform.), 2647 and 2551 (Amine Salt/St.), 1492 (Amine/St.), 802 (Aromatic/Deform.) cm-1.

A solution of the pure pitolisant monohydrochloride in acetone may be evaporated and dried at 70° C. for 17 hours, to provide crystals of Form I for use in DSC analyses.

Example 2. Preparation and Analysis of Pitolisant Hydrochloride Polymorph Form II Pitolisant hydrochloride polymorph Form II was provided by heating samples of pitolisant hydrochloride in a Differential Scanning calorimetry (DSC) apparatus, according to the following protocols.

Protocol 1

With reference to FIG. 2, a sample of the Form I crystals from Example 1 was placed in a DSC apparatus, and the sample was heated from 20° C. to 150° C. at a rate of 10° C./min, revealing an endothermic peak with an onset of 116.3° C. and peak of 118.0° C. that corresponds to the crystalline sample melting (trace (1), peak (a1)). The melted sample was then cooled from 150° C. to 0° C. at a rate of 10° C./min, revealing a double exothermic phenomenon with onsets at 72.0° C. and 70.7° C. (trace (2), peaks (b) and (c)), which can be attributed to recrystallization of Form I.

The sample was then heated from 0° C. to 140° C. at a rate of 10° C./min, causing an endothermic peak corresponding to melting of the known phase at 117.2° C. (trace (3), peak (a3)). A quench from the melt was then performed by cooling the sample from 140° C. to 0° C. at a rate of 200° C./min, resulting in a broad exothermal signal which can be attributed to crystallization of the starting phase (see trace (4) signal (d) in FIG. 2). The sample was held for 2 minutes at 0° C. The sample was then heated again, from 0° C. to 140° C. at a rate of 10° C./min 2), resulting in the expected peak at about 118° C. corresponding to melting of the known crystalline phase (see trace (5) peak (a5) in FIG. 2).

Next, the sample was cooled from 140° C. to 73° C. at a rate of 10° C./min (trace (6)), which is slightly above the temperature of the previously observed double endothermic peaks (peaks (b) and (c)), and the sample was maintained at this temperature for 4 minutes. With reference to FIG. 2 (cont.), the sample was heated from 73° C. to 150° C. at a rate of 10° C./min, resulting in an endothermic peak with an onset of 93.1° C. and peak of 94.4° C. (trace (7), peak (II)). This corresponds to the melting of a polymorph distinct from Form I (e.g., compare peak (II) with peaks (a1), (a3), (a5), (a9)), and is therefore attributed to a new polymorphic form of pitolisant hydrochloride, referred to herein as Form II.

The sample containing Form (II) was subsequently cooled from 150° C. to 15° C., resulting in a double endothermic peak (trace (8), peaks (f) and (g)). These peaks can be attributed to the crystallization of Form II, immediately followed by crystallization of Form I or a polymorph transformation. Finally, the last step involved heating the sample from 15° C. to 145° C. at a rate of 10° C./min, revealing an endothermic peak caused by Form (I) melting as evidenced by the expected onset of about 117° C. (trace (9) peak (a9)).

Protocol 2

With reference to FIG. 3, pitolisant hydrochloride was placed in a DSC apparatus, and the sample was heated from 20° C. to 130° C. at 10° C./min, resulting in an endothermic peak with a long shoulder at 111.9° C., with an additional signal at 106.6° C. (trace (1), peak p (1) and p (1')). By cooling the sample from 130° C. back down to 20° C. at a rate of 10° C./min, an exothermic event was observed that is attributed to crystallization of the sample (trace (2) peak (b2)). The sample was heated again, from 20° C. to 130° C. at 10° C./min resulting in three endothermic events: a small signal at around 106° C., a large peak with an offset at 109.5° C., and a sharp peak at 117.8° C., which corresponds to the melting of Form I (trace (3), peaks (p3'), (p3), and (a3)). The sample was then cooled from 130° C. to 72° C. at a rate of 10° C./min and held at 72° C. for 1 hour (trace (4)). The sample was then heated from 72° C. to 130° C. at a rate of 10° C./min, resulting in an endothermic peak at 93.7° C., which can be attributed to the melting of Form II (trace (5) peak (II)). This melting point is consistent with the melting point observed for Form II during Protocol 1 (e.g., compare peak (II) in FIG. 2 with peak (II) in FIG. 3).

With reference to FIG. 3 (cont.), the sample was then cooled down from 130° C. to 50° C. at a rate of 10° C./min, resulting in an exothermal event at around 70° C. (trace (6) peak (b6)), and was heated from 50° C. back to 130° C. causing an endothermic peak at 117.5° C., corresponding to Form (I) melting (trace (7) peak (a7). The sample was then cooled down to 72° C. and maintained for 1 hour (trace 8), heated again to 82° C. (trace (9) and finally cooled down to 20° C. (trace 10). No thermal event was observed during these last steps (represented by traces (8)-(10)). The sample was immediately removed from the aluminium pan and analyzed by XRPD, described in Example 3.

Summary

Protocols 1 and 2 evidence the obtention of form II as follows:

In a DSC apparatus, a melt sample of pitolisant hydrochloride was cooled from 140° C. to 73° C. at a rate of 10° C./min (trace (6) on FIG. 2), which is slightly above the temperature of the previously observed double endothermic peaks (peaks (b) and (c)), and the sample was maintained at this temperature for 4 minutes. With reference to FIG. 2 (cont.), the sample was heated from 73° C. to 150° C. at a rate of 10° C./min, resulting in an endothermic peak with an onset of 93.1° C. and peak of 94.4° C. (trace (7), peak (II)). This corresponds to the melting of a polymorph distinct from Form I (e.g., compare peak (II) with peaks (a1), (a3), (a5), (a9)), and is therefore attributed to a new polymorphic form of pitolisant hydrochloride, referred to herein as Form II.

Or Alternatively

In a DSC apparatus, a melt sample of pitolisant hydrochloride was cooled down from 130° C. to 72° C. and maintained for 1 hour (trace 8), heated again to 82° C. (trace (9) and finally cooled down to 20° C. (trace 10). No thermal event was observed during these last steps (represented by traces (8)-(10)). The sample was immediately removed from the aluminium pan and analyzed by XRPD, described in Example 3.

Protocols 1 and 2 each resulted in the formation of a second polymorphic form of pitolisant hydrochloride (Form II), with a melting temperature of about 93° C., as determined by DSC. The melting point of Form II is lower the known polymorph of pitolisant hydrochloride (i.e., Form I), which has a melting point of about 117° C.

Example 3. X-Ray Powder Diffraction (XRPD) Study

Following the DSC study described in Protocol 2 of Example 2, the sample was removed from the aluminium pan and analyzed by XRPD, according to the XPRD methods described above. The diffraction pattern from this sample was obtained, and is provided in FIG. 1 (see diffractogram A). The sample was then stored for 10 months at room temperature enclosed between polymer foils, and then analyzed again by XRPD, providing diffractogram B which is overlaid in FIG. 1. From these studies, the characteristic peaks of crystalline Form II were identified, which are indicated by dashed lines in FIG. 1 and are also listed below in Table 2.

TABLE 2

| Positions of diffraction signals corresponding to Form II. | | |
|---|---|---|
| 2θ Position (°) | Intensity (counts) | Relative Intensity (%) |
| 15.81 | 169 | 9.2 |
| 16.79 | 1133 | 61.5 |
| 18.24 | 1226 | 66.6 |
| 18.49 | 960 | 52.2 |
| 18.82 | 129 | 7.0 |
| 19.30 | 248 | 13.5 |
| 20.07 | 343 | 18.6 |
| 21.08 | 1841 | 100.0 |
| 25.11 | 1287 | 69.9 |

EQUIVALENTS

Those skilled in the art will recognize or be able to ascertain using no more than routine experimentation many equivalents to the specific embodiments disclosed herein. Those of ordinary skill in the art will appreciate that various changes or modifications to this description may be made without departing from the spirit or scope of the present disclosure, as defined in the following claims.

The invention claimed is:

1. A crystalline form of a compound represented by Formula (I):

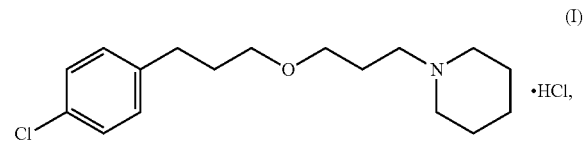 [SMILES: Clc1ccc(CCCOCCCN2CCCCC2)cc1]

(I)

characterized by having an X-ray diffraction pattern comprising each of the following peaks, in terms of 2-theta (2θ): 16.8°, 18.2°, 18.5°, 21.1°, and 25.1° (±) 0.2°.

2. The crystalline form of claim 1, characterized by having an X-ray diffraction pattern comprising each of the following peaks (2θ): 15.8°, 16.8°, 18.2°, 18.5°, 18.8°, 19.3°, 20.1°, 21.1°, and 25.1° (±) 0.2°.

3. The crystalline form of claim 1, characterized by having an X-ray diffraction pattern substantially as shown in pattern A of FIG. 1.

4. The crystalline form of claim 1, further characterized by having an endothermic peak with an onset between about 90° C. and about 97° C., as obtained by differential scanning calorimetry (DSC).

5. The crystalline form of claim 4, wherein the onset is between about 92° C. and about 95° C.

6. The crystalline form of claim 4, wherein the endothermic peak is about 94° C.

7. The crystalline form of claim 1, characterized by having a melting point between about 90° C. and about 95° C.

8. The crystalline form of claim 1, characterized by having a DSC thermogram comprising an endothermic peak substantially as shown by peak (II) of FIG. 2.

9. The crystalline form of claim 1, characterized by having a DSC thermogram comprising an endothermic peak substantially as shown by peak (II) of FIG. 3.

10. The crystalline form of claim 1, wherein the X-ray diffraction pattern does not comprise a combination of peaks (2θ) at 11.2°, 19.9°, 20.7°, and 34.1° (±) 0.2°.

11. A pharmaceutical composition comprising the crystalline form of claim 1, and a pharmaceutically acceptable excipient.

12. The pharmaceutical composition of claim 11, wherein the pharmaceutically acceptable excipient is selected from the group consisting of colloidal silicon dioxide, crospovidone, magnesium stearate, microcrystalline cellulose, polyethylene glycol, polyvinyl alcohol, talc, and titanium dioxide.

13. A dosage form comprising the crystalline form of claim 1.

14. The dosage form of claim 13, wherein the dosage form is a tablet, caplet, or capsule.

15. The crystalline form of claim 4, wherein the endothermic peak is about 97° C.

* * * * *